(12) United States Patent
Peppi et al.

(10) Patent No.: US 11,771,876 B2
(45) Date of Patent: Oct. 3, 2023

(54) SYSTEM FOR INNER EAR DRUG DELIVERY VIA TRANS-ROUND WINDOW MEMBRANE INJECTION

(71) Applicant: The Charles Stark Draper Laboratory, Inc., Cambridge, MA (US)

(72) Inventors: Marcello Peppi, Medford, MA (US); Ernest Soonho Kim, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 16/581,169

(22) Filed: Sep. 24, 2019

(65) Prior Publication Data

US 2021/0085939 A1   Mar. 25, 2021

(51) Int. Cl.
*A61M 31/00* (2006.01)
*A61M 5/14* (2006.01)
*A61M 5/142* (2006.01)

(52) U.S. Cl.
CPC .......... *A61M 31/00* (2013.01); *A61M 5/1409* (2013.01); *A61M 5/14212* (2013.01); *A61M 2210/0612* (2013.01); *A61M 2210/0618* (2013.01); *A61M 2210/0662* (2013.01); *A61M 2210/1003* (2013.01); *A61M 2210/1064* (2013.01)

(58) Field of Classification Search
CPC .......... A61B 2017/00787; A61F 11/00; A61M 31/00; A61M 37/00; A61M 2210/0662; A61M 2210/0668; A61M 2210/0675; A61M 5/14; A61M 5/1409; A61M 5/1408; A61M 5/142; A61M 5/14212; A61M 5/16827; A61M 5/3294; A61M 3/005; A61M 25/0026; B01F 5/00
See application file for complete search history.

(56) References Cited

U.S. PATENT DOCUMENTS

| | | | | |
|---|---|---|---|---|
| 4,191,183 A | * | 3/1980 | Mendelson | A61M 5/1408 141/107 |
| 2001/0027819 A1 | * | 10/2001 | Wages | A61M 25/0029 138/116 |
| 2004/0002740 A1 | * | 1/2004 | Lee | A61B 17/3478 607/9 |
| 2008/0025950 A1 | * | 1/2008 | Prestwich | A61P 43/00 424/93.1 |

(Continued)

*Primary Examiner* — Nilay J Shah
(74) *Attorney, Agent, or Firm* — Foley & Lardner LLP (57) ABSTRACT

A system for the delivery of therapeutic substances to cavities of a patient. The system can include a handpiece tool coupled with a pump. The handpiece tool can include a shaft including a first portion of a channel coupled to a multi-input tubing. The handpiece tool can include an angled portion coupled with the shaft. The handpiece tool can include a second portion of the channel, wherein the angled portion positions a tip portion within a cavity, wherein the tip portion projects from the angled portion and includes an outlet and a third portion of the channel. The handpiece tool can include a collar a distance from the outlet, the collar configured to control a distance the tip portion projects. The handpiece tool can include a mixing chamber configured to receive the components of the drug and output the mixed drug via the third portion of the channel.

20 Claims, 10 Drawing Sheets

(56) References Cited

U.S. PATENT DOCUMENTS

2012/0101478 A1* 4/2012 Stroumpoulis ....... A61M 3/005
604/518
2017/0367892 A1* 12/2017 Kim ..................... A61M 31/00

* cited by examiner

SYSTEM FOR INNER EAR DRUG DELIVERY VIA TRANS-ROUND WINDOW MEMBRANE INJECTION

BACKGROUND OF THE DISCLOSURE

Delivery of therapeutics to the human inner ear can be challenging for clinicians. Two anatomic "windows" from the middle ear to the inner ear exist, the oval and round windows. Each of these windows include a semi-permeable membrane. Drug delivery to the inner ear requires that a therapeutic substance cross one of these membranes.

SUMMARY OF THE DISCLOSURE

Inner ear drug delivery can use diffusion to cross one or both of the membranes of the anatomic windows to the inner ear. Relying on diffusion across a membrane poses a number of difficulties. For example, diffusing therapeutic substances across the membranes can introduce a lack of precision in terms of dose delivery. Relying on diffusion can also limit the size and characteristics of therapeutic substance's molecules because, for example, not all substances can diffuse across the membranes. Another example challenge is that the round window membrane permeability can vary between patients or during states of inflammation. The handpiece of the present disclosure can overcome these challenges by delivering a therapeutic substance directly to the inner ear.

According to at least one aspect of the disclosure, a handpiece tool includes a shaft that includes a first portion of a microfluidic channel and is configured to connect with a multi-input tubing to receive a plurality of fluids, such as from a pump. The handpiece tool can include an angled portion coupled with the tool shaft. The angled portion can include a second portion of the microfluidic channel. The angled portion can be configured to position a tip portion of the handpiece within a cavity of a patient. The tip portion can project from the angled portion and can include an outlet and a third portion of the microfluidic channel. The handpiece can include a collar coupled with the tip portion. The collar can be a predetermined distance from the outlet. The collar can be configured to control a distance the tip portion projects into the cavity.

In some implementations, the handpiece tool can include a mixing chamber. The mixing chamber can include a mixing element to mix fluids as the fluids flow along the length of the mixing chamber. The pump can include a second pump configured to flow a second fluid from a second reservoir into the mixing chamber to mix with the first fluid in the mixing chamber. The first pump can be a first pump type, and the second pump can be a second pump type different than the first pump type. The first pump can be configured to flow the first fluid and the second fluid into the mixing chamber.

In some implementations, the first pump can be a lead screw-driven mini syringe pump, a 3-actuator pump, a mini peristaltic pump, or a pneumatic/hydraulic-driven pump. In some implementations, the collar can be configured to seat with a round window of a patient's cochlea.

According to at least one aspect of the disclosure, a method can include establishing a fluidic coupling between a handpiece tool and a pump using a tubing. The handpiece tool can include a microfluidic channel coupled to the tubing to receive a plurality of fluids responsive to operation of one or more pumps of the pump. The method can include inserting a tip of the shaft of an angled portion of the handpiece tool into a cavity of a patient. A collar coupled with the tip a predetermined distance from an outlet of the tip is configured to control a distance the tip projects into the cavity of the patient. The method can include mixing, by a mixing chamber of the handpiece tool, the plurality of fluids received from the multi-input tubing to provide a mixed fluid. The method can include outputting the mixed fluid via the microfluidic channel through the outlet of the tip to within the cavity of the patient.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways as the described concepts are not limited to any particular manner of implementation. Examples of specific implementations and applications are provided primarily for illustrative purposes.

The present disclosure discusses a handpiece tool for fluid delivery, such as in a drug delivery system. The system can include a handpiece and a pump (e.g., a micropump). The system can be used to deliver fluids, such as fluids that can include one or more drugs, to a cavity within the patient. For example, the handpiece can be inserted into the middle ear via a surgical tympanotomy approach. The handpiece can enable a controlled injection of a therapeutic substance directly through the round window membrane and into the inner ear. The direct delivery of the therapeutic substance to the inner ear can enable the delivery of a precise amount of therapeutic substance into the inner ear. Because the therapeutic substance is delivered directly to the inner ear, the delivery of the therapeutic substance is not subject to limitations on molecule size and inconsistent diffusion rates that are present when therapeutic substances are diffused across the round window membrane.

Figure 1:
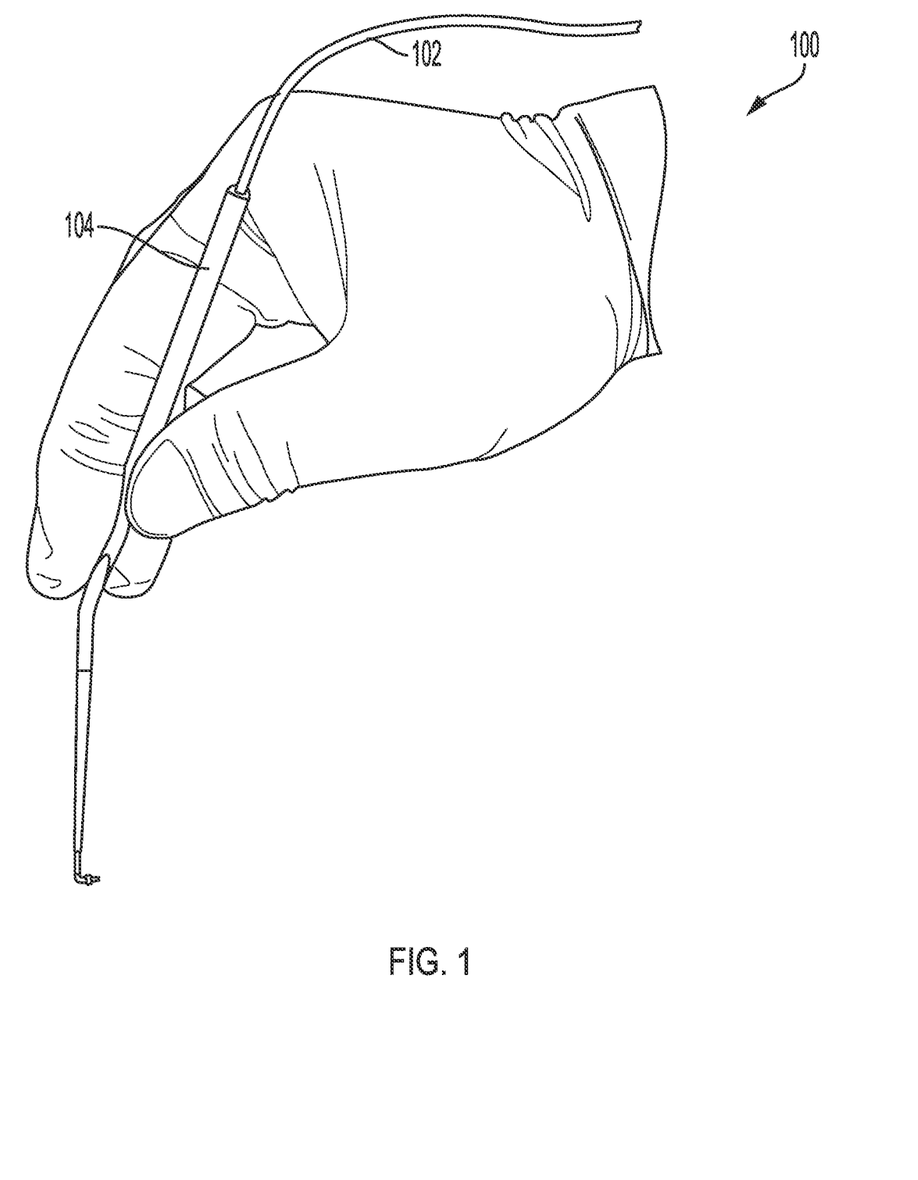
FIG. 1 illustrates an example fluid delivery system.

FIG. 1 illustrates an example fluid delivery system 100. The system 100 includes a handpiece 104 for the delivery of the drug to the body cavity. The handpiece 104 is described in greater detail in relation to FIGS. 3-9, among others. The handpiece 104 can be coupled with a pump (e.g., pump 162 depicted in FIG. 2) via tubing 102. The tubing 102 can be a fixed or static length, such as 15 centimeters, 12 inches, 1 meter, etc. The tubing 102 length can refer to a multi-input tubing fluidly coupled to one or more pumps 162.

The system 100 is configured to deliver drug, therapeutic agents, fluids, or other materials to a human's natural cavities. The injected substances can generally be referred to as fluids. The cavities can include, but are not limited to, the inner ear, ocular cavity, spinal cavity, oral cavity, anal cavity, urinary cavity, and/or cervix cavity. The system 100 can control the level of drug penetration, amount of drug diffusion, volume of drug injected, and the flow rate of the injected drug.

Figure 2:
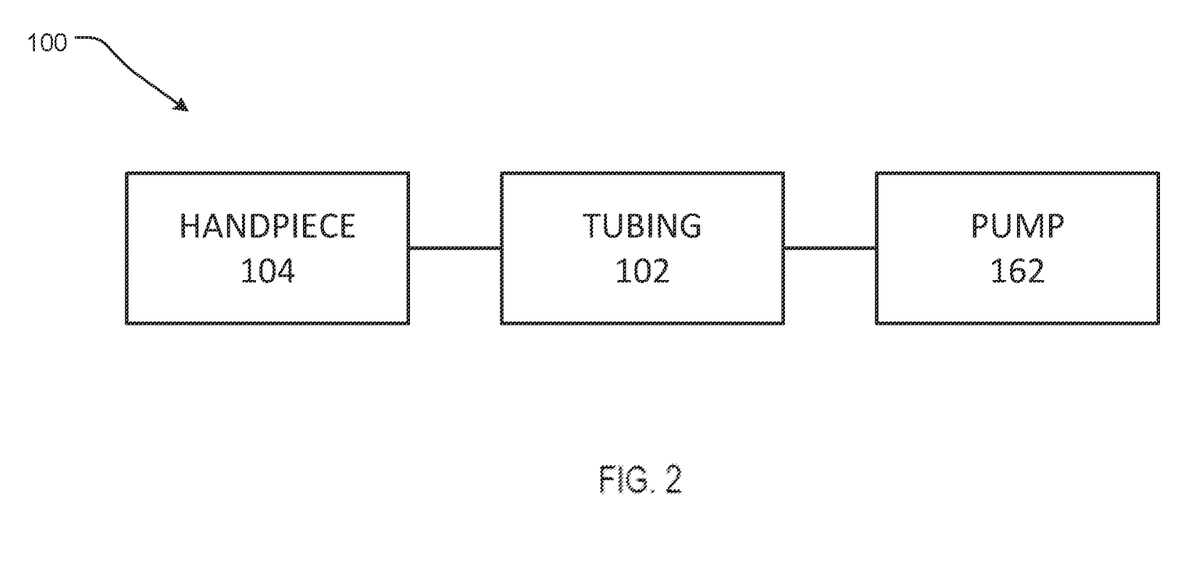
FIG. 2 illustrates a block diagram of an example system for use in the system illustrated in FIG. 1.

FIG. 2 illustrates an block diagram of the system 100 in which a pump 162 is provided to connect with the tubing 102 and handpiece 104 (e.g., to cause the handpiece 104 to deliver drugs to the cavity of the body). The pump 162 can be a small, self-contained pump. The pump 162 can be a wearable pump. The pump 162 can be self-contained by internally including a power system to power the pump and one or more reservoirs to store the fluid to be injected. The pump 162 can include a strap that enables the pump 162 to mount or attach onto a surface. Mounting the pump 162 can increase stability of the pump 162. The pump 162 can be a distance (or proximity) from the handpiece 104, such as 10 centimeters ("cm"), 20 cm, or 30 cm from the handpiece 104. The proximity can refer to the length of a tubing 102. The proximity of the pump 162 to the handpiece 104 can limit the amount of dead volume within the tubing 102 between the pump 162 and the handpiece 104. The proximity of the pump 162 to the handpiece 104 can also improve the precision and control of drug penetration, drug diffusion, volume injection, and flow rate.

The pump 162 can include an interface (e.g., user interface) which can receive commands to control the pump 162, for example, to display a status of the pump 162 and information about the status of the delivery of the drug to the patient. The pump 162 can include a plurality of inputs, which can be physical inputs (e.g., buttons, sliders), virtual inputs (e.g., inputs provided via a display or touchscreen). The interface can receive commands to control the pump from one or more inputs. For example, via the inputs, a user can navigate the interface of the pump 162 to, for example, determine the status of the pump 162 and select injection parameters. The status of the pump 162 can include an amount of remaining drugs in the reservoirs or an amount of drugs delivered via the pump 162, current power level of the power supply. The injection parameters can include fluid injection rate, total allowed fluid injection volume, selection of which fluid to inject, the sequence or order of fluid injection, and withdrawal rate. The pump 162 can include pump reservoirs to deliver drugs from one or more reservoirs to the handpiece 104 via the tubing 102. Each reservoir can store a different type of drug than other reservoirs. The reservoirs can be situated within the pump 162. The reservoirs can be external to the pump 162. The pump 162 can include a strap to mount the pump 162 onto a surface (e.g. floor, ceiling, pole, etc.). The pump 162 can be equipped to a portion of a user (e.g. wrist, torso, arm, or other part of a body) to enable ergonomic use of the system and to leave the user's hands free to perform other tasks during the injection of the fluid.

The pump 162 can include a processor to control the function of the pump 162. The processor can be any type of single or multi-core processor or special purpose logic circuitry such as an FPGA (field programmable gate array) or an ASIC (application specific integrated circuit). In some implementations, the processor can include one or more antennas to enable the processor (and pump 162) to communicate with external devices. For example, the processor can communicate with an external controller or remote that can be used to start, stop, or pause the flow of fluid to the handpiece 104. The external controller or remote can be operated by a second user other than the user operating the pump 162. The pump 162 can include a power supply that can include batteries, such as rechargeable batteries, or a capacitor that can supply power to the components of the pump 162. The power supply can include an alternating current (AC) to direct current (DC) converter. For example, the pump 162 can be plugged into an AC mains. The power supply can convert the power from the AC mains into DC power that can be used by the processor and other components of the pump 162.

The pump 162 can include a plurality of pumps 162. For example, the pump 162 can include a different pump 162 for each of the reservoirs. Each of the different pumps 162 can be the same type of pump or a different type of pump. The pump 162 can include one or more of a lead screw-driven mini syringe pump, 3-actuator pump, mini peristaltic pump, or pneumatic/hydraulic-driven pump. The pneumatic/hydraulic-driven pump can be driven by an external pressure source that can be coupled with the pump 162 to drive the pump 162. In some implementations, different configurations of the pump 162 with different pumps types can be selected based on the drug or fluid within the reservoirs. For example, a first pump type can be used for fluids with a relatively high viscosity and a second pump type can be used for fluids with a relatively low viscosity. In some implementations, one or more pumps 162 can withdraw a fluid from the cavity. These pumps 162 can be referred to as vacuum pumps. The pumps 162 can withdraw the fluid into a separate reservoir configured to store the withdrawn fluid. In some implementations, the vacuum pump can be an independent pump that is configured to only withdraw fluid from the cavity. In some implementations, the pumps 162 can be configured to operate in multiple directions such that during a first time period or phase the pumps 162 can pump fluid into the cavity, and during a second time period or phase the pumps 162 can withdraw fluid from the cavity. In some implementations, a first pump acting as a vacuum pump can operate at the same time as a second pump flows fluid into a cavity such that the amount of fluid removed by first pump is substantially the same as the amount of fluid injected by the second pump.

The handpiece 104 can be used to deliver a drug to the patient (e.g., based on the drug being driven by the pump 162). The drug can be generally referred to as a fluid. The drug can be a gel. The fluid can be a two-part gel. For example, a first part of the gel can be stored in a first reservoir, and a second part of the gel can be stored in a second reservoir. The system 100 can mix the two parts of the gel just prior to injection via the handpiece 104. The fluid can include large molecules such as proteins, antibodies, genes, DNA, RNA, particles, viruses, liposomes, nanoparticles, microspheres, and magnetic drug delivery particles. Each fluid in the different reservoirs can be the same or different fluids. In some implementations, one or more reservoirs can be initially empty, and the pump 162 can be used to draw fluid from the patient which can be stored in the reservoirs.

Figure 3:
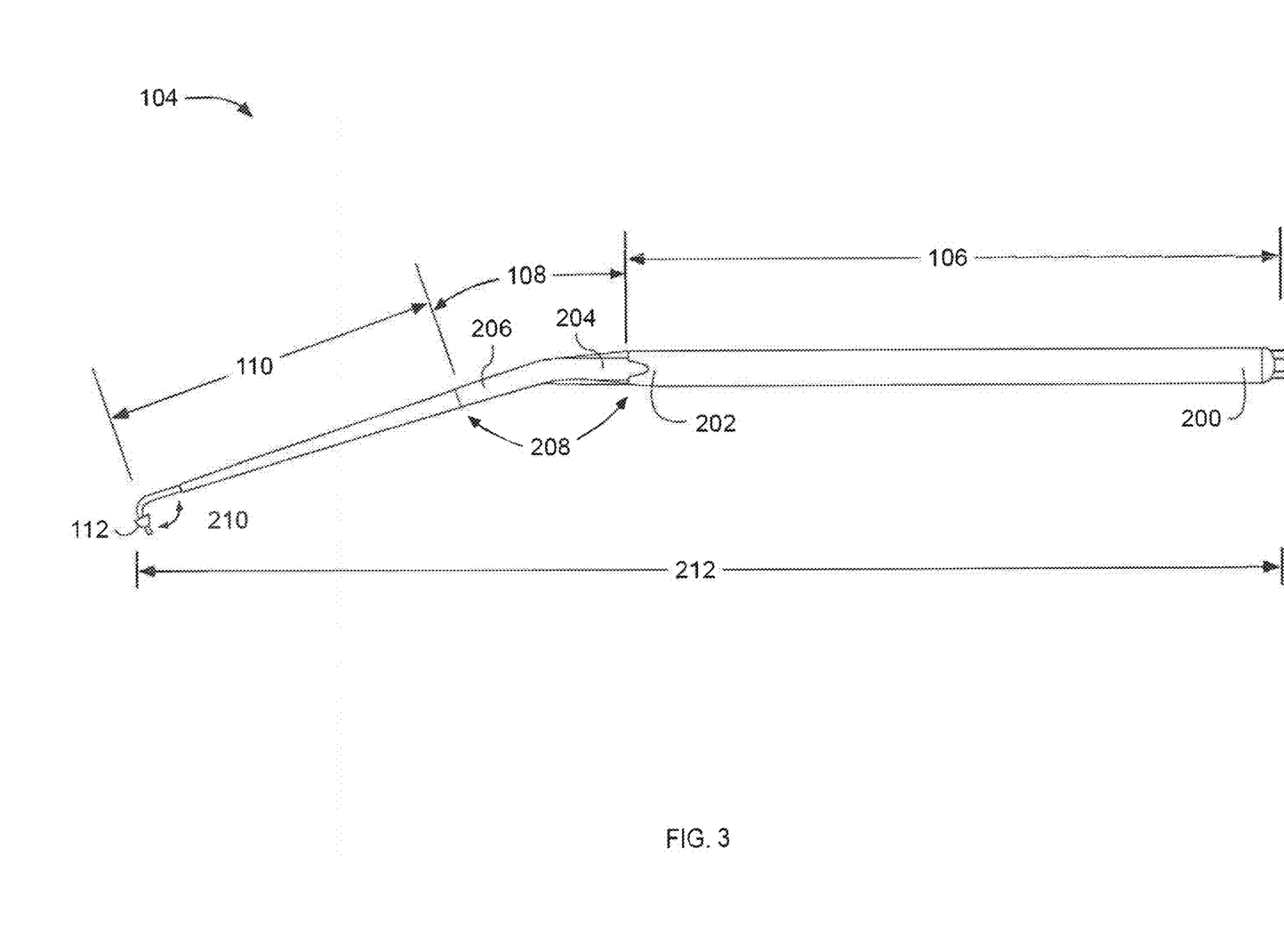
FIG. 3 illustrates a side view of the example handpiece illustrated in FIG. 1.

FIG. 3 illustrates a side view of an example handpiece 104 for delivering fluid to a patient's cavity such as the inner ear. The fluid can be any therapeutic substance or therapeutic agent. The handpiece 104 includes a tool shaft 106, an angled portion 108, and a tip portion 110. The tip portion 110 can also include a collar 112. The tip portion 110 can be used to pierce membranes or other thin tissue. For example, the handpiece 104 can be inserted into the ear canal of the patient for the transcanal delivery of fluid to the cochlea via the round window. The tip portion 110 can be used to pierce the round window membrane to enable fluid to be delivered to the cochlea. In some implementations, the handpiece 104 can at least a portion of transparent material through which flow of drug or components of the drug are viewable to a user. The transparent material can refer to a see through material, such as glass, acrylic, or plastic.

The handpiece 104 includes the tool shaft 106, the angled portion 108, and the tip portion 110. A surgeon can use the tool shaft 106 to hold and manipulate the handpiece 104 and position of the tip portion 110. The outer surface of the tool shaft 106 can include knurling to enable a better grip of the handpiece 104 by the surgeon. The tool shaft 106 includes a proximal end 200 and a distal end 202. The tool shaft 106 can have a diameter of about 4 mm, 5 mm, or about 6 mm. The tool shaft 106 can have a length of between about 90 mm and about 162 mm, between about 90 mm and about 130 mm, or between about 100 mm and about 120 mm. In some implementations, the length of the tool shaft 106 is 110 mm.

The distal end of the tool shaft 106 is coupled with the proximal end 204 of the angled portion 108. The tip portion 110 is coupled with the distal end 206 of the angled portion 108. The angled portion 108 is angled to enable the tip portion 110 to traverse the ear canal in a minimally invasive procedure and reach the round window. The angled portion 108 forms an angle 208 between the tool shaft 106 and the tip portion 110. The angle 208 can be about 170° and about 90°, between about 170° and about 110°, between about 170° and about 120°, between about 170° and about 140°, or between about 165° and about 155°. The angle 208 can be defined as the angle between a longitudinal axis of the tool shaft 106 and a longitudinal axis of the tip portion 110. The angle 208 is configured to enable transcanal positing of the tip portion 110 at a patient's round window. The angle 208 can be selected to enable a surgeon to position the tip portion 110 at the round window and provide the surgeon visual access to the ear canal.

The tip portion 110 can be coupled with the distal end 206 of the angled portion 108. The distal portion of the tip portion 110 can be angled. The angle 210 can be between about 70° and about 140°, between about 75° and about 130°, between about 90° and about 120°, between about 100° and about 120°, or between about 110° and about 120°. For example, the angle 210 can be about 105°, 106°, 107°, 108°, 109°, 110°, 111°, 112°, 113°, 114°, 115°, 116°, 117°, 118°, 119°, or 120°. The angle 210 can be selected to position the distal portion of the tip portion 110 substantially perpendicular to the round window when the handpiece 104 is inserted through the ear canal. The angle 210 can be selected based on the anatomical configuration of the patient's inner and middle ear. For example, the surgeon can select a handpiece 104 with an appropriate angle 210 based on the position and angle of the round window and the round window niche. In some implementations, the surgeon can determine which angle 210 to select using CT or MRI images of the middle and inner ear. The handpiece 104 can be manufactured with different angle 210 configurations. In some implementations, the surgeon can bend the tip portion 110 to alter the angle 210 during a procedure.

The tip portion 110 can include a collar 112. The collar 112 can be configured to seat with a cavity of a patient including a round window of a patient's cochlea, for example. The collar 112 can seal the round window once the tip portion 110 pierces the round window membrane. The collar 112 can also control the depth the end of the tip portion 110 can be inserted into the cochlea. The collar 112 can include a medical-grade silicone. The collar 112 can be substantially domed or semi-spherical in shape. The diameter of the collar 112, at the collar's widest, can be between about 0.5 mm and about 3 mm, between about 0.5 mm and about 2.5 mm, between about 1 mm and about 2 mm, or between about 1.5 mm and about 2 mm.

The handpiece 104 can have an overall length 212 between about 130 mm and about 170 mm, between about 140 mm and about mm, or between about 140 mm and about 162 mm. While described as different portions, the tool shaft 106, the angled portion 108, and the tip portion 110 can each be manufactured as single or multiple pieces. For example, the handpiece 104 can include one, two, or three separate pieces. The handpiece 104 can be separable at the interface between any of the tool shaft 106, the angled portion 108, and the tip portion 110. In some implementations, the interface between the tool shaft 106, the angled portion 108, and the tip portion 110 does not indicate that the portions are separable. For example, the tool shaft 106, the angled portion 108, and the tip portion 110 can be manufactured as a single piece. In other implementations, the angled portion 108 and the tool shaft 106 can form a first piece, and the tip portion 110 can form a second piece. In some implementations, the handpiece 104 is reusable. In other implementations, the handpiece 104 is disposable. The handpiece 104 can be manufactured from medically-approved sterilizable materials. For example, the handpiece 104 can be manufactured from 316 stainless steel or a sterilizable plastic.

Figure 4:
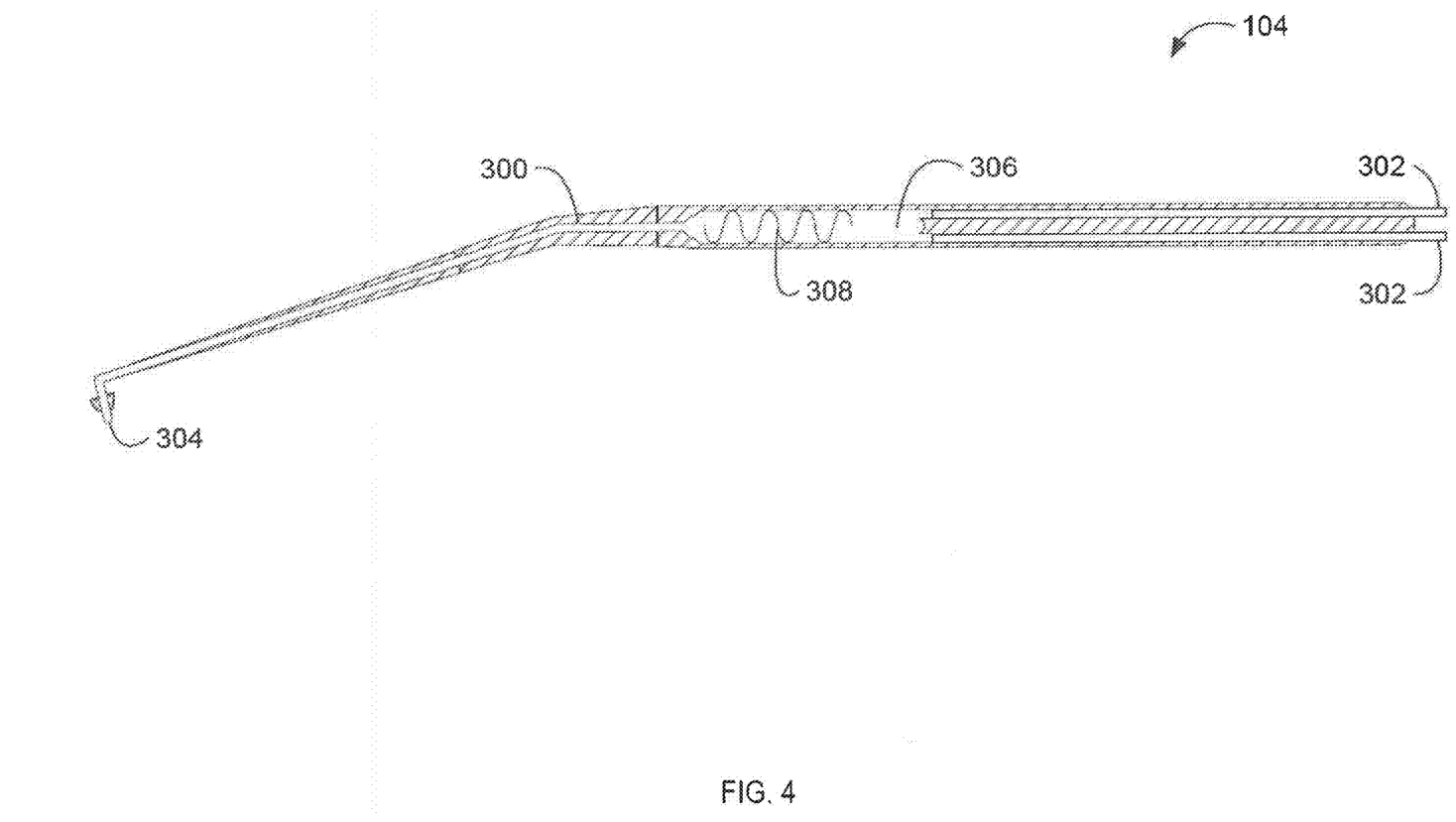
FIG. 4 illustrates a cross-sectional view of the example handpiece illustrated in FIG. 1.

FIG. 4 illustrates a cross-sectional view of the example handpiece 104. The handpiece 104 can include a microfluidic channel 300. The handpiece 104 can include a first and a second inlet 302 to receive two or more components of a drug. The handpiece 104 can include an outlet 304 to output a mixed drug to within a cavity of a patient. The handpiece 104 can include a mixing chamber 306. The mixing chamber 306 can include one or more mixing elements 308. In some implementations, the first and the second inlet 302 and the outlet 304 can refer to portions of the microfluidic channel 300.

The handpiece 104 can include an inlet 302 for each of the reservoirs. For example, each inlet 302 can be coupled with an independent reservoir via a different tubing 102 (or an input of a multi-input tubing 102) or a different internal lumen of the tubing 102. The inlets 302 can deliver their respective fluids (or components) from an independent reservoir to the mixing chamber 306. The fluids can refer to different drugs. The fluids from the independent reservoirs can mix within the mixing chamber 306. For example, the fluids within the independent reservoirs can be activated when the fluids are mixed together. In some implementations, it can be advantageous to mix and activate the fluids just prior to delivery of the fluids to the patient.

The handpiece 104 can include a mixing chamber 306. The different fluids (e.g., a first and second part of a two-part or multipart gel) from the independent inlets 302 can mix within the mixing chamber 306 before entering the microfluidic channel 300. The mixing chamber 306 can include mixing elements 308 to mix the fluids that enter the mixing chamber 306. The mixing elements 308 can include helical mixers that mix the fluids as the fluids are pushed (or flow) along the length of the mixing chamber 306. The mixing elements 308 can include ribs, protrusions, fins, or other elements that can create non-laminar flow within the mixing chamber 306 to mix the fluids within the mixing chamber 306.

The microfluidic channel 300 can have a gauge of about 22. The microfluidic channel's gauge can be between about 12 and 28, between about 16 and about 24, between about 18 and about 22, or between about 20 and 22. The microfluidic channel 300 can have a dead volume of between about 10 µL and about 25 µL, between about 15 µL and about 25 µL, or between about 20 µL and about 25 µL.

Figure 5:
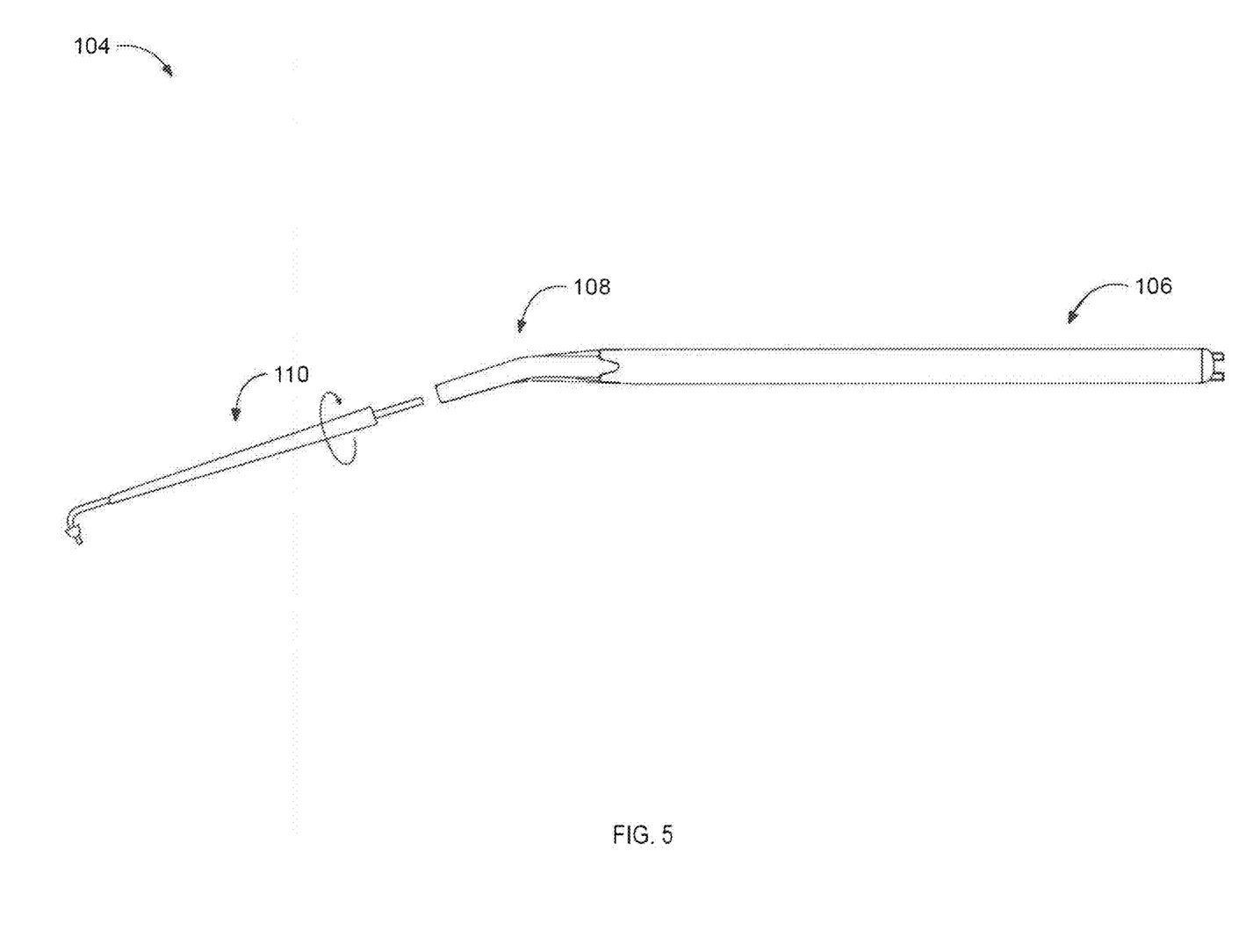
FIG. 5 illustrates a side view of the example handpiece illustrated in FIG. 1.

The microfluidic channel 300 can include different portions. For example, each of the tool shaft 106, angled portion 108, and the tip portion 110 can include a different portion of the microfluidic channel 300. The different portions can be a single channel or continuous channel. In some implementations, the microfluidic channel 300 is separable at the interface between one or more of the portions. In some implementations, the microfluidic channel portions are separable near the interface between the different portions of the handpiece 104. For example, the microfluidic channel portion within the tip portion 110 can extend past the tip portion 110 (as illustrated in FIG. 5), and the microfluidic channel portion within the angled portion 108 can stop prior to the distal end 206 such that a portion of the microfluidic channel extending from the tip portion 110 can be received by the angled portion 108. In some implementations, the handpiece 104 can include a plurality of microfluidic channels 300. For example, the handpiece 104 may not include a mixing chamber 306 and the different microfluidic channels 300 can each be coupled with a different one of the inlets 302. In some implementations, a second microfluidic channel 300 can be used to evacuate fluid from the cavity.

FIG. 5 illustrates a side view of the example handpiece 104. In some implementations, one or more of the portions of the handpiece 104 are separable from one another. FIG. 5 illustrates an example handpiece 104 with a separable tip portion 110. The tip portion 110 can be separated from the tool shaft 106 and the angled portion 108 to facilitate sterilization of the handpiece 104. The tip portion 110 can be separable from the angled portion 108 to enable the tip portion 110 to be recoupled with the angled portion 108 at a different rotational angle. The tip portion 110 can be rotated with respect to the angled portion 108 without separating the tip portion 110 from the angled portion 108. The tip portion 110 can be rotated with respect to the angled portion 108 to provide the surgeon with improved access to the round window. For example, the surgeon can adapt the default position of the tip portion 110 to account for variability between patient anatomies. The handpiece 104 can include gaskets or o-rings at the interface between the separable portions. The separable portions can be coupled together with snap-on connectors, friction-fit or press-fit connections, or Luer lock connections.

Figure 6:
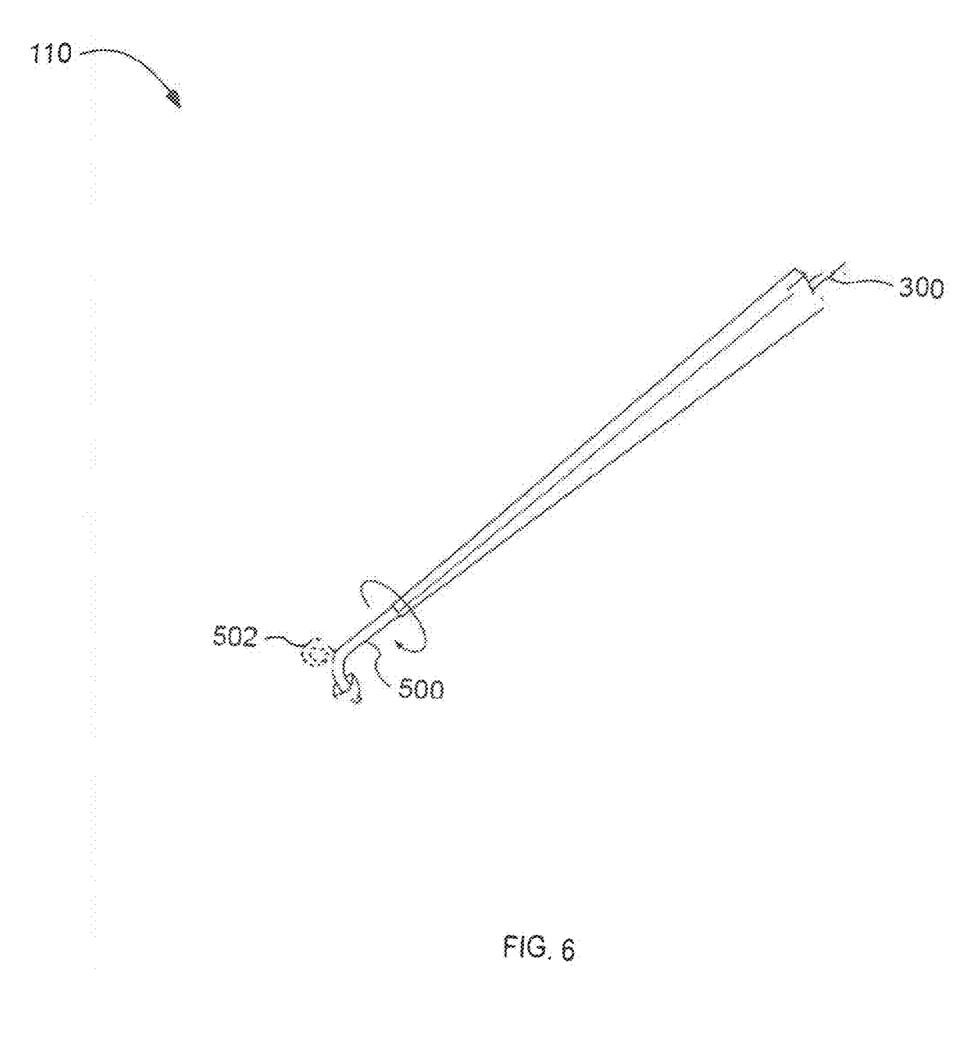
FIG. 6 illustrates an example tip portion for the handpiece illustrated in FIG. 1.

FIG. 6 illustrates an example tip portion 110 for the example handpiece 104. The tip portion 110 illustrated in FIG. 6 is separated from the angled portion 108 and the tool shaft 106 of the handpiece 104. The tip portion 110 can include a tip 500. The tip 500 can be a portion of the microfluidic channel 300 extending from the body of the tip portion 110. In some implementations, all of the tip portion 110 can be rotated with respect to the angled portion 108. In other implementations, the tip 500 can be rotated within the tip portion 110. In either example, the tip 500 can be rotated from the position illustrated in FIG. 5 to a second position 502, illustrated by the dashed lines.

Figure 7:
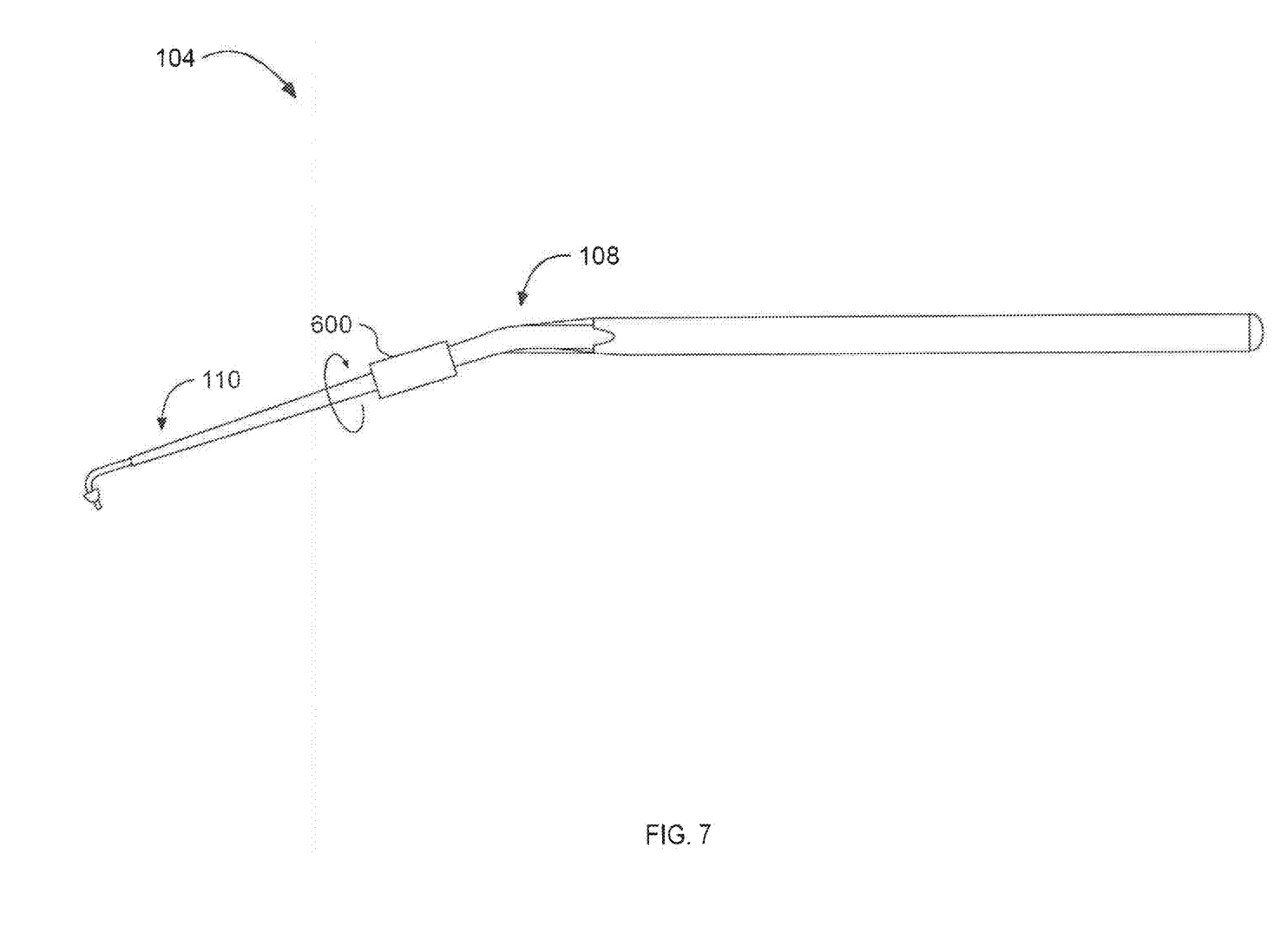
FIG. 7 illustrates an example handpiece with a compression fitting.

FIG. 7 illustrates an example handpiece 104 with a compression fitting 600. The compression fitting 600 can be a knurled nut. The compression fitting 600 can couple the angled portion 108 with the tip portion 110. The compression fitting 600 can be loosened to enable the tip portion 110 to rotate with respect to the angled portion 108. Once the surgeon selects a degree of rotation, the surgeon can tighten the compression fitting 600 to lock the degree of rotation between the angled portion 108 and the tip portion 110 in place. In other implementations, the tip portion 110 and the angled portion 108 can be held together with a friction-fit that enables the tip portion 110 to be rotated with respect to the tip portion 110.

Figure 8:
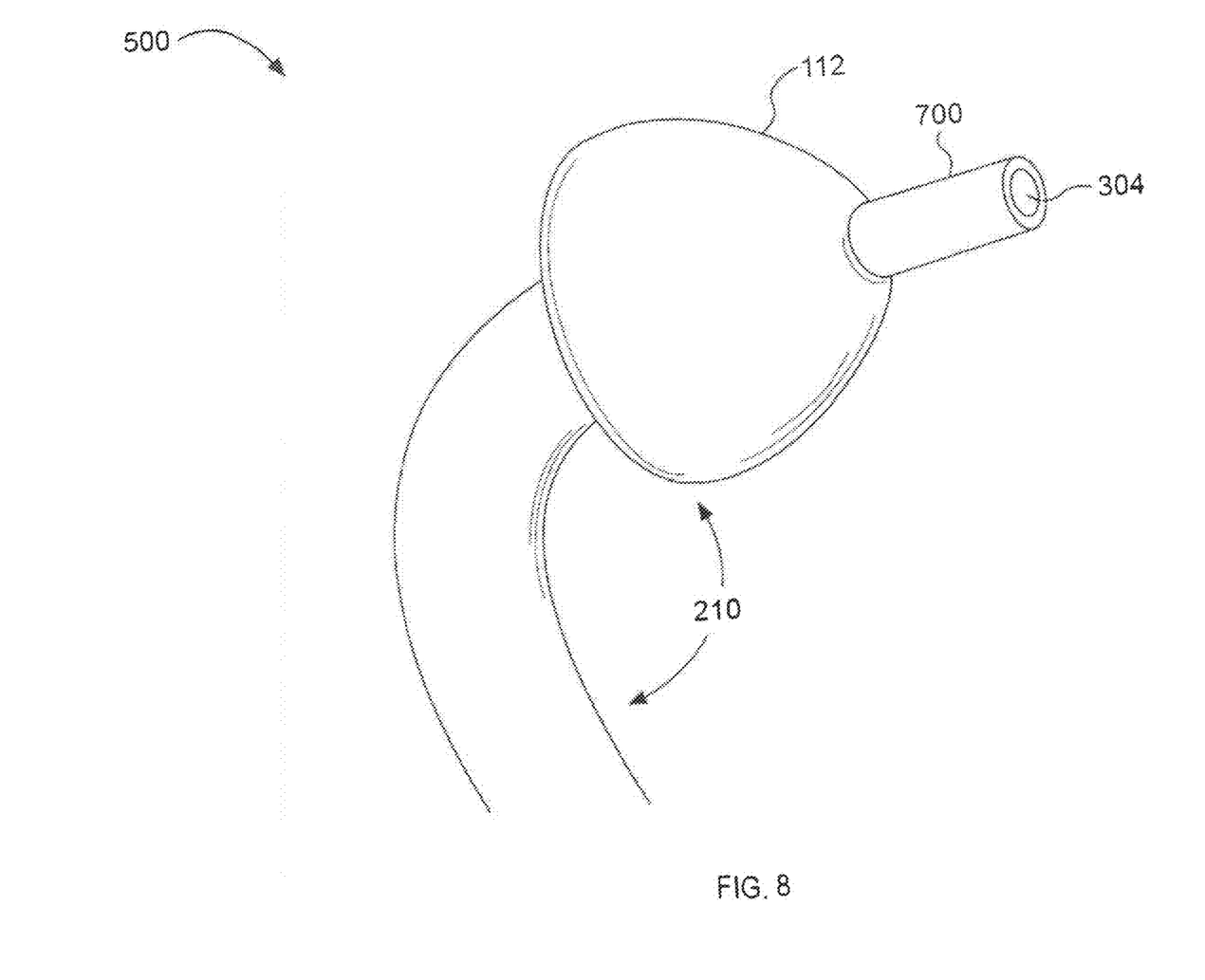
FIG. 8 illustrates an enlarged view of the tip of the example handpiece illustrated in FIG. 1.

FIG. 8 illustrates an enlarged view of the tip 500 of the example handpiece 104. The tip 500 can include a needle end 700. The needle end 700 includes the outlet 304. The needle end 700 can be a blunt end or can be beveled to form a point. The needle end 700 can be configured to pierce the round window membrane. The needle end 700 extends past the collar 112 by a length between about 1 mm and about 4 mm, between about 2 mm and about 3 mm, or between about 2.5 mm and about 3 mm. For example, the needle end 700 can have a length of 2.7 mm. The needle end 700 can have a gauge size between about 25 and about 30, between about 26 and about 30, or between about 27 and about 30.

Once the collar 112 is seated into the round window, only the needle end 700 projects into the cochlea. The collar 112 can control the depth the needle end 700 projects into the cochlea. The needle end 700 can prevent the needle end 700 from projecting too far into the cochlea and damaging the cochlea. The collar 112 can properly position the outlet 304 within the cochlea so that the therapeutic substance properly disperses through the cochlea. For example, if the outlet 304 is positioned too shallow into the cochlea, the therapeutic substance can concentrate near the round window and not disperse through the cochlea. If the outlet 304 is positioned too deep into the cochlea, the needle end 700 can cause damage or trauma to the cochlea. In some implementations, the tip 500 is manufactured from a malleable material such that a surgeon can bend the tip 500 to alter the angle 210. The collar 112 can be coupled with the tip 500 with an adhesive. In some implementations, the tip 500 can include a groove in which the collar 112 is seated.

Figures 9A, 9B:
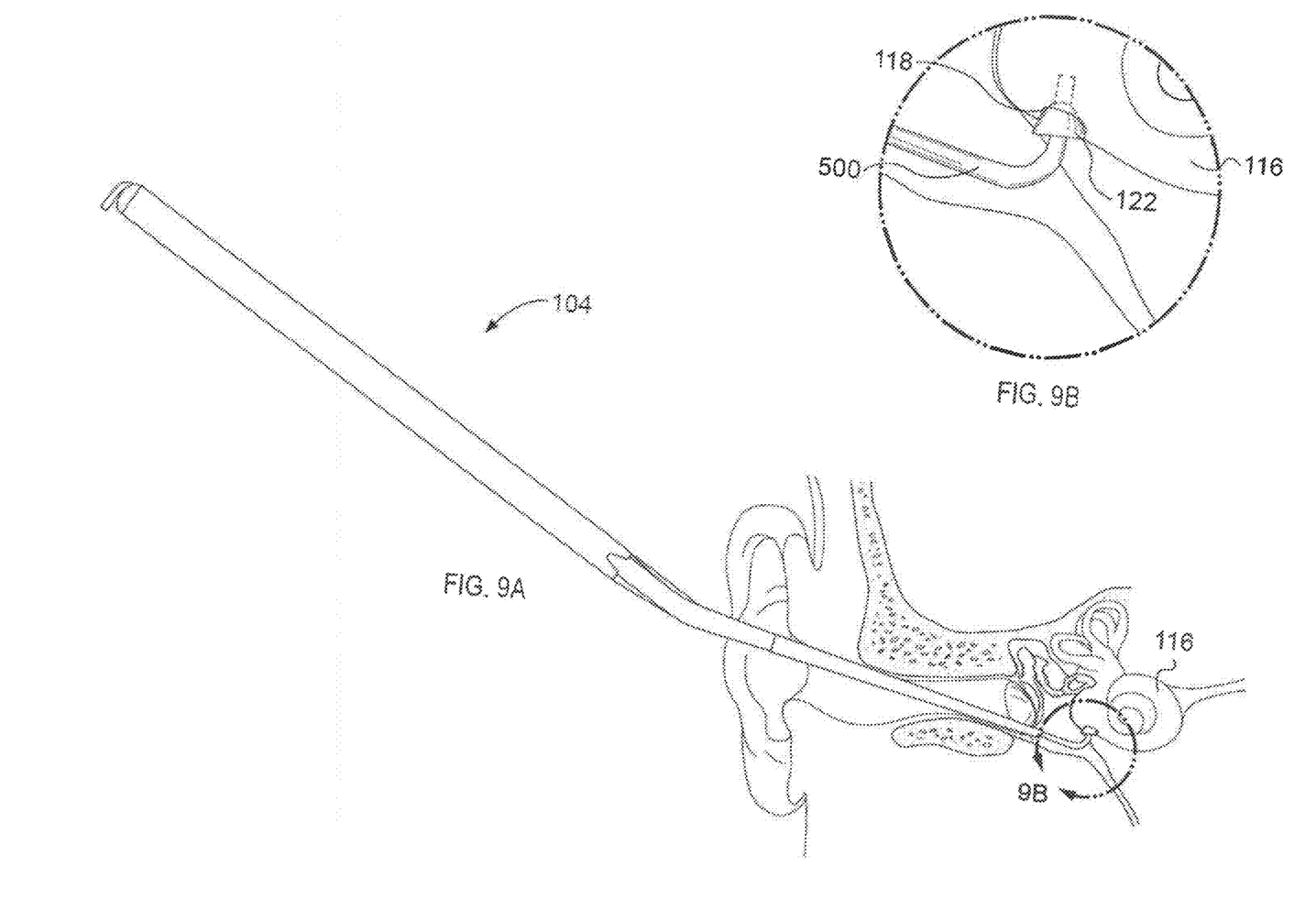
FIGS. 9A and 9B illustrates the tip of the example handpiece inserted into a round window.

FIGS. 9A and 9B illustrate the tip 500 inserted into the round window. FIG. 9A illustrates the handpiece 104 inserted through the ear canal with the tip 500 inserted into the round window 118. FIG. 9B illustrates an enlarged view, from FIG. 9A, of the tip 500 inserted into the round window 118. The tip 500 can be used to pierce the round window membrane. The tip 500 can be inserted into the round window 118. The collar 112 can be seated into the round window 118 and seal the round window 118 as fluid is injected into the cochlea 116. The collar 112 is tapered from a diameter smaller than the diameter of the round window 118 to a diameter that is wider than the diameter of the round window 118. When the collar 112 is depressed against the round window 118, the collar 112 can occlude the round window 118. The collar 112 can also be used to control the insertion depth of the tip 500 into the cochlea 116. For example, the collar 112 can prevent the tip 500 from being inserted into the cochlea past the collar 112. The portion of the collar 112 with a diameter wider than the diameter of the round window 118 can substantially stop the tip 500 from farther insertion of the tip 500 into the cochlea 116. Moving the collar 112 towards the outlet 120 of the tip 500 reduces the depth to which the tip 500 can be inserted. The collar 122 can prevent the tip 500 from being inserted too far into the cochlea 116.

Figure 10:
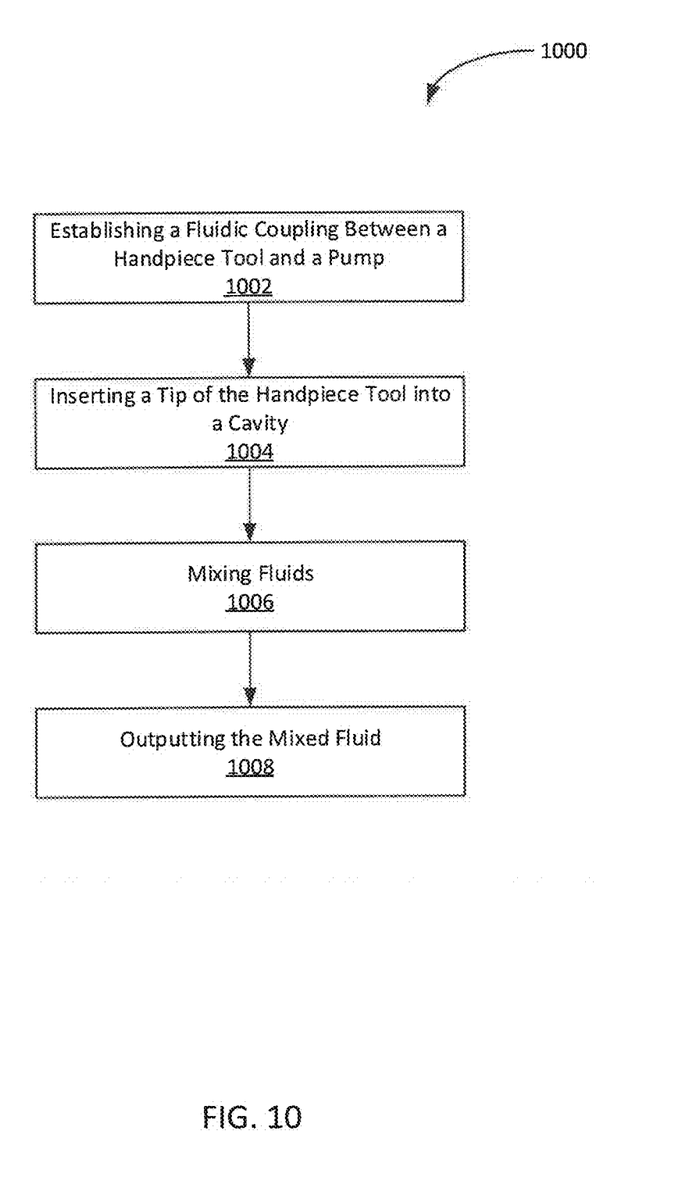
FIG. 10 illustrates a block diagram of an example method to flow a fluid into the cochlea with the system illustrated in FIG. 1.

FIG. 10 illustrates a block diagram of an example method 1000 to flow a fluid into the cochlea. The method 1000 can include establishing a fluidic coupling between a pump and a handpiece tool connected via a multi-input tubing (ACT 1002). The method 1000 can include inserting a tip of the shaft of an angled portion of the handpiece tool into a cavity of a patient (ACT 1004). The method 1000 can include mixing a plurality of fluids received from the multi-input tubing by a mixing chamber of the handpiece tool (ACT 1006). The method 1000 can include outputting the mixed fluid via the microfluidic channel through the outlet of the tip to within the cavity of the patient (ACT 1008).

As set forth above, the method 1000 can include establishing a fluidic coupling between a pump and a handpiece tool connected via a multi-input tubing (ACT 1002). Also referring to FIGS. 1-9, the system 100 can include a pump 162 that is coupled with a handpiece 104 to flow fluid through the handpiece 104 and out an outlet of the handpiece 104.

The pump 162 can include one or more reservoirs that each can include a different fluid. The fluid can be a therapeutic, drug, or other active agent. The pump 162 can include one or more pumps that flow the fluid from the reservoirs to the handpiece 104 (or handpiece tool) via a tubing 102. The handpiece 104 can include a microfluidic channel coupled to the multi-input tubing to receive components of a drug via one or more reservoirs responsive to one or more pumps 162 of the pump 162.

The handpiece 104 can be any of the handpieces described herein. For example, the handpiece 104 can include a tool shaft that includes a first distal end, a first proximal end, a first fluidic channel, and a first longitudinal axis. The handpiece 104 can include an angled portion that can include a second distal end, a second proximal end coupled with the first distal end, a second fluidic channel in communication with the first fluidic channel, and a second longitudinal axis defining an obtuse angle with the first longitudinal axis. The handpiece 104 can include a tip portion projecting from the angled portion and including an outlet and a third fluidic channel in communication with the second fluidic channel. The handpiece 104 can include a collar coupled with the tip portion. The handpiece 104 can include a mixing chamber 306 that can mix the plurality of fluids received at the inlets 302 from the pump 162. The mixing chamber 306 can include mixing elements that can facilitate the mixing of the fluids.

The method 1000 can include inserting a tip of the shaft of an angled portion of the handpiece 104 into a cavity of a patient (ACT 1004). The method 100 can insert the tip by piercing a round window membrane. The round window membrane can be pierced with the tip portion of the handpiece 104. For example, the provided handpiece 104 can be inserted through the ear canal. The handpiece angled portion 108 can be configured to enable transcanal access of the round window. The tip 500 of the tip portion 110 can be angled to position the needle end 700 substantially perpendicular to the round window and round window membrane. The needle end 700 can be pressed against the round window membrane to pierce the round window membrane. The collar 112 can couple with the tip a predetermined distance from an outlet of the tip is configured to control a distance the tip projects into the cavity of the patient. The collar 112 can prevent the needle end 700 from projecting too far into the cochlea and causing damage to the cochlea. The collar 112 can seat into the round window to seal the round window as the fluid is injected into the cochlea. Based on the patient's anatomy, a surgeon can set a rotational offset between the tip portion and the angled portion of the handpiece 104 to enable the needle end 700 to access the round window. Also based on the patient's anatomy, the surgeon can set the angle 210 between the needle end 700 and the tip portion such that the outlet 304 is positioned substantially perpendicular to the round window and round window membrane. CT or MRI scans of the patient's middle and inner ear can be conducted. The surgeon can measure the anatomical angles of the patient's inner and middle ear to select the angle 210 of the tip portion 110. Also, based on the CT or MRI scans, the surgeon can select the length of the needle end 700 such that when the collar 112 is seated into the round window the outlet 304 is properly positioned within the cochlea. The proper position of the outlet 304 can be a depth into the cochlea that does not cause damage to the cochlea but enables distribution of the fluid through the cochlea.

The method 1000 can include mixing the fluids received from the multi-input tubing by a mixing chamber 306 of the handpiece 104 (ACT 1006). The mixing chamber 306 can include mixing elements that can facilitate the mixing of the fluids. The mixing elements can refer to components of the mixing chamber 306 to expedite the process of mixing the components of the drug, such as a propeller, heat generator, or a compressor. For example, the pump 162 can transfer a first component and a second component from reservoirs to a mixing chamber 306 of the handpiece 104 via tubes 102 corresponding to each component. The mixing chamber 306 can receive the first component and the second component via inlets 302. The mixing chamber 306 can mix the first component and the second component into a third component (or a mixed drug), for example, to output a mixed drug to within the cavity of a patient. In some implementations, the method 1000 can include activating the pump 162 or the mixing chamber 306 to mix components of a drug while the tip portion 110 is projected into the cavity of a patient.

The method 1000 can include outputting the mixed fluids via the microfluidic channel through the outlet of the tip to within the cavity of the patient (ACT 1008). The pump 162 can pump the fluid (or drug) from a reservoir, through the microfluidic channel 300, and into the cochlea via outlet 304. The method 1000 can include drilling, or otherwise forming, a ventilation hole in the stapes footplate. The ventilation hole can enable the release of pressure from the cochlea as the pump flows the fluid into the cochlea. In some implementations, the method 1000 can include withdrawing a fluid from the cochlea as fluid is pumped into the cochlea to maintain a constant pressure within the cochlea.

As described above, a method similar to the method 1000 can be performed to inject a fluid into other cavities of a patient. In some implementations, the system can be used to inject fluids into an ocular cavity. For example, the handpiece tip can be inserted into the inferior temporal quadrant 3.5 mm posterior to the limbus and a drug from the system's reservoirs can be injected into the vitreous cavity. After retracting the tip of the handpiece 104, the transcleral perforation can be closed with a 50-μm-thick cyanoacrylate bioadhesive-fixed polyimide patch.

In some implementations, the system 100 can be used to inject fluids into a spinal cavity. The system 100 can be used to deliver drugs into the epidural space via the interlaminar, caudal, or transforaminal approach. During the interlaminar approach, the handpiece tip can be placed into the back of the epidural space and the drug can be delivered over a wider area. During the caudal approach, the sacral hiatus can be used to enable the handpiece tip to be placed into the very bottom of the epidural space. Once injected, the drug can spread over several spinal segments and cover both sides of the spinal canal. During the transforaminal approach, the handpiece tip can be placed alongside the nerve as it exits the spine and the fluid can be injected into the "nerve canal." The fluid can then travel up the nerve canal and into the epidural space from the side. This method can enable for a more concentrated delivery of the fluid into one affected area.

In some implementations, the system 100 can be used to inject fluids into a rectal cavity. During rectal surgery, the handpiece tip can be inserted into the rectal cavity to reach the rectal mucosa. Upon insertion of the handpiece tip into the mucosa, fluid can be delivered and the handpiece can be retracted. Areas nearby pathological tissue can be injected to limit spreading of the disease. Prior to the drug delivery, contrast dye can be premixed with the drug to confirm that the area medication is traveling into the desired area.

In some implementations, the system 100 can be used to inject fluid into the nasal cavity. For example, the drug can be injected into the bilateral maxillary sinus by inserting the handpiece tip into the superior meatus location of the olfactory epithelium. After reaching the area near the olfactory epithelium, a gel can be injected via the handpiece 104 that will release the gel's drug directly into the brain.

In some implementations, the system 100 can be used to inject fluids into the vaginal cavity. During cervical surgery, the handpiece tip can be inserted into the cervix cavity. Areas nearby cancerous tissue can be injected with the insertion of the handpiece tip to deliver fluids adjacent to the cancerous tissue either before resection (to reduce tumor size) or after resection (to reduce the risk of recurrence). Prior to the drug delivery, contrast dye can be used to confirm that the medication is traveling into the desired area.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A handpiece tool, comprising:
a shaft extending along a longitudinal shaft axis from a first shaft end to a second shaft end, the shaft comprising a first portion of a microfluidic channel configured to connect with a multi-input tubing to receive a plurality of fluids, the first portion comprising a first inlet channel defined within the shaft by a channel portion of a wall of the shaft and extending from a first inlet to connect with the multi-input tubing and a second inlet channel defined within the shaft by the channel portion of the wall of the shaft and extending from a second inlet to connect with the multi-input tubing;

an angled portion extending from the second shaft end of the shaft along a longitudinal angle axis at an angle to the longitudinal shaft axis, the angled portion comprising a second portion of the microfluidic channel, wherein the angled portion is configured to position a tip portion within a cavity of a patient, wherein the tip portion projects from the angled portion and comprises an outlet and a third portion of the microfluidic channel;

a collar coupled with the tip portion at a predetermined distance from the outlet, the collar configured to control a distance the tip portion projects into the cavity of the patient; and a mixing chamber in the shaft, the mixing chamber contiguous with and extending straight from the channel portion of the wall of the shaft, the mixing chamber between the first portion and the second shaft end of the shaft, the mixing chamber configured to receive, via the multi-input tubing, the first inlet channel, and the second inlet channel, the plurality of fluids to provide the plurality of fluids to a mixing element in the mixing chamber, the mixing element between the channel portion and a portion of the mixing chamber narrowing to the second portion of the microfluidic channel, the mixing element configured to mix the plurality of fluids to provide a mixed fluid and output the mixed fluid via at least the third portion of the microfluidic channel through the outlet into the cavity of the patient.

2. The handpiece tool of claim 1, wherein the mixing element includes at least one of a rib, a protrusion, or a fin.

3. The handpiece tool of claim 1, wherein the plurality of fluids comprises a plurality of multipart gels.

4. The handpiece tool of claim 1, wherein the plurality of fluids comprise a plurality of drugs.

5. The handpiece tool of claim 1, wherein the multi-input tubing comprises a plurality of tubing.

6. The handpiece tool of claim 1, wherein the multi-input tubing is fluidly coupled to a plurality of pumps, the plurality of pumps configured to pump the plurality of components to the multi-input tubing and to withdraw a cavity fluid from the cavity.

7. The handpiece tool of claim 1, wherein each input of the multi-input tubing is fluidly coupled to an independent reservoir of a pump.

8. The handpiece tool of claim 1, wherein the handpiece tool comprises a portion of transparent material through which flow of the plurality of fluids or the mixed fluid is viewable.

9. The handpiece tool of claim 1, wherein the collar is configured to be seated within the cavity of the patient comprising a round window of a patient's cochlea.

10. The handpiece tool of claim 1, wherein the handpiece tool is configured to mix the plurality of fluids and deliver the mixed fluid via the outlet while the tip portion is projected into the cavity of the patient.

11. A method, comprising:
establishing a fluidic coupling between a handpiece tool and a pump using a multi-input tubing, the handpiece tool comprising a shaft extending along a longitudinal shaft axis from a first shaft end to a second shaft end, the shaft comprising a microfluidic channel comprising a first inlet channel and a second inlet channel each defined in the shaft by a channel portion of a wall of the shaft and coupled to the multi-input tubing to receive a plurality of fluids responsive to operation of one or more pumps of the pump;

inserting a tip of an angled portion extending along a longitudinal angle axis at an angle to the longitudinal shaft axis from the second shaft end into a cavity of a patient, wherein a collar coupled with the tip at a predetermined distance from an outlet of the tip is configured to control a distance the tip projects into the cavity of the patient;

mixing, by a mixing element of a mixing chamber in the shaft, the mixing chamber contiguous with the wall and extending straight from the channel portion of the wall, the mixing chamber between the first shaft end and the second shaft end, the plurality of fluids received from the multi-input tubing to provide a mixed fluid, the mixing element between the channel portion and a portion of the mixing chamber narrowing to the second portion of the microfluidic channel; and outputting the mixed fluid via the microfluidic channel through the outlet of the tip to within the cavity of the patient.

12. The method of claim 11, wherein the mixing element comprises at least one of a rib, a protrusion, or a fin.

13. The method of claim 11, wherein the plurality of fluids comprises multipart gels.

14. The method of claim 11, wherein the plurality of fluids comprise a plurality of drugs.

15. The method of claim 11, wherein the multi-input tubing comprises a plurality of tubing.

16. The method of claim 11, wherein each input of the multi-input tubing is fluidly coupled to an independent reservoir of the pump.

17. The method of claim 11, wherein the handpiece tool comprises a portion of transparent material through which flow of the plurality of fluids or the mixed fluid is viewable.

18. The method of claim 11, wherein the collar is configured to be seated within the cavity of the patient comprising a round window of a patient's cochlea.

19. The method of claim 11, further comprising mixing the plurality of fluids and delivering the mixed fluid via the outlet while the tip is projected into the cavity of the patient.

20. A handpiece tool, comprising:
a straight shaft extending along a first shaft end to a second shaft end along a first longitudinal axis, the shaft comprising a first inlet channel and a second inlet channel, the first inlet channel and the second inlet channel extending partially through the shaft from the first shaft end towards the second shaft end, the shaft comprising a mixing chamber contiguous with the first inlet channel and the second inlet channel and positioned between (i) the first inlet channel and the second inlet channel and (ii) the second shaft end, the shaft comprising a mixing element in the mixing chamber, the mixing element comprising at least one of a rib, a protrusion, or a fin, the mixing chamber extending straight from the first inlet channel and the second inlet channel in a direction towards the second shaft end past the mixing element and narrowing past the mixing element, the first inlet channel and the second inlet channel each having a respective inlet at the first shaft end to couple with a multi-input tubing, the first inlet channel, the second inlet channel, and the mixing chamber forming a first portion of a microfluidic channel;

an angled portion extending from the second shaft end of the shaft along a second longitudinal angle axis at an angle to the first longitudinal axis, the angled portion forming a second portion of the microfluidic channel, wherein the angled portion is configured to position a tip portion within a cavity of a patient, wherein the tip portion projects from the angled portion and comprises an outlet and a third portion of the microfluidic channel; and a collar coupled with the tip portion at a predetermined distance from the outlet, the collar configured to control a distance the tip portion projects into the cavity of the patient.

* * * * *